United States Patent [19]

Knobel

[11] 4,273,620

[45] Jun. 16, 1981

[54] PROCESS FOR RECONCENTRATING MOIST GLYCOL

[75] Inventor: Walter Knobel, Kerpen, Fed. Rep. of Germany

[73] Assignee: Davy International AG, Frankfurt, Fed. Rep. of Germany

[21] Appl. No.: 919,234

[22] Filed: Jun. 26, 1978

[30] Foreign Application Priority Data

Jun. 25, 1977 [DE] Fed. Rep. of Germany ....... 2728745

[51] Int. Cl.³ .................... B01D 3/00; B01D 53/26; C07C 29/26
[52] U.S. Cl. ........................ 203/18; 203/21; 203/22; 203/23; 203/39; 203/49; 203/DIG. 8; 55/32; 159/29; 202/176; 202/177; 202/233; 202/234
[58] Field of Search ............ 203/18, 49, 42, 47, 203/39, DIG. 8, 21, 22, 25, 27; 52/32; 202/176, 177, 233, 234; 159/16 R, 29

[56] References Cited

U.S. PATENT DOCUMENTS

| 3,105,748 | 10/1963 | Stahl | 203/18 |
| 3,321,890 | 5/1967 | Barnhart | 55/32 |
| 3,370,636 | 2/1968 | Francis et al. | 159/16 R |
| 3,450,603 | 6/1969 | Meyers et al. | 203/18 |
| 3,824,177 | 7/1974 | Honerkamp et al. | 203/18 |
| 3,841,382 | 10/1974 | Gravis et al. | 203/18 |
| 3,867,112 | 2/1975 | Honerkamp et al. | 55/32 |
| 4,010,065 | 3/1977 | Alleman | 203/18 |

Primary Examiner—Wilbur L. Bascomb, Jr.
Attorney, Agent, or Firm—Bernard & Brown

[57] ABSTRACT

Reconcentration of moist glycol, which has been used to dry natural gas, by heating the moist glycol with flue gas from a reboiler and by thereafter stripping water from the moist glycol with the dried flue gas or with a hydrocarbon gas by-product of the natural gas being dried.

8 Claims, 3 Drawing Figures

PROCESS FOR RECONCENTRATING MOIST GLYCOL

BACKGROUND OF THE INVENTION

This invention relates to an improved process for drying gases such as natural gas by treatment of such gas with a glycol drying agent. More particularly, this invention relates to improvements in the methods for reconcentrating glycol drying agents which have been used to remove water from natural gas streams.

When gases, more particularly natural gas, are dried with a glycol, more particularly triethylene glycol, water vapor is absorbed from the gas and a water-containing glycol is formed. If this glycol is to be reused for gas-drying purposes, the water-containing glycol must be reconcentrated to remove most of the water therefrom. Accordingly, the water-containing glycol is generally heated and the major part of the water is thereby vaporized and separated out, thereby forming a concentrated glycol of low water content. This reconcentrated glycol is returned into the gas-drying stage. Mere heating of the moist glycol cannot be used to accomplish complete drying of the glycol, since at maximum heating temperatures for glycols (about 205° C. with triethylene glycol), a drying of only up to about 99.0 percent glycol is realized. When operating continuously, higher heating temperatures lead to a partial thermal decomposition of the triethylene glycol, so that the advantage of the higher reconcentration is lost due to increased expense for the replacement of the glycol. Efforts have been made, however, to increase the concentration of the glycol still further, since the residual moisture of the gas dried with glycol proportionately decreases as the concentration of the glycol used for the drying is increased. It is thus possible, for example, when using a 99.9 percent triethylene glycol (instead of one which is only 99 percent) and a contact temperature with the gas to be dried of 20° C., to reduce the dew point of the gas from about −20° C. to about −40° C.

It is also known to cool natural gas with a content of liquid hydrocarbons in the dried or undried state down to temperatures of, for example, −30° to 0° C. and thereby to condense and separate out the liquid hydrocarbons and the moisture possibly contained in the gas. With undried natural gas, dried glycol can be sprayed as a hydrate inhibitor into the stream of natural gas prior to cooling and moist glycol and liquid hydrocarbon are separated out as condensate after the expansion of the natural gas to pipeline pressure. This moist glycol, like the moist glycol which is formed from drying of the natural gas by absorption with glycol, is again reconcentrated and is used for spraying or for absorption purposes.

It is also known to improve still further the degree of drying of the thermally reconcentrated glycol by stripping the glycol being reconcentrated with a heated dry gas. Serving as stripping gas is dried natural gas, which is heated in the reboiler and is then brought into contact with the preconcentrated glycol discharging from the reboiler (Cf. U.S. Pat. No. 3,105,748). The disadvantage of this process consists in that a part of the valuable product gas in consumed for stripping purposes. The stripping gas charged with the water vapor is generally blown off into the atmosphere or burnt. To avoid this, the stripping gas can also be recirculated. In this case, the stripping gas is cooled and an aqueous phase is deposited in a separator. The stripping gas as thus dried returns, together with supplementary gas, into the stripping section of the reconcentration plant (Cf. U.S. Pat. No. 3,867,112). It is true that the consumption of stripping gas and the contamination of the air are smaller in this case, but the expense for the working up and recirculation of the stripping gas is considerable.

Finally, it is also known to carry out the absorption treatment of a moist, hydrocarbon-containing natural gas with a mixture of glycol and liquid hydrocarbon. The moist glycol and the liquid hydrocarbon phase charged with volatile hydrocarbons are separated after being heated and the hydrocarbon phase is combined with the hot glycol in the stabilizer section of the regeneration plant. The volatile hydrocarbons are thereby driven off from the liquid hydrocarbon phase and cause a further concentration of the pre-concentrated glycol, while the stabilized hydrocarbon liquid returns together with the dried glycol into the absorption stage (Cf. U.S. Pat. No. 3,321,890). With this operating procedure, it is necessary to have the joint circulation of glycol and hydrocarbon liquid between the absorption stage and the regeneration stage, and this is a procedure which generally causes the glycol to reach a foaming condition during the regeneration.

This invention has for its object provision of a new process for the thermal reconcentration of glycol, using stripping gas, with which the disadvantages of the former processes operating with the use of stripping gas are avoided. In other words, the use of dried natural gas as stripping gas and also the working up and recirculation of stripping gas and the recirculation of hydrocarbon between absorption stage and regeneration stage can be avoided.

SUMMARY OF THE INVENTION

The present invention relates to a process whereby moist glycol which has been used to remove moisture from a natural gas stream is reconcentrated. Reconcentration is accomplished by first heating the moist glycol with reboiler flue gas to a temperature of about 100° to 210° C. and by thereafter stripping additional moisture from the heated glycol with either dried flue gas from the reboiler or with a hydrocarbon gas by-product of the natural gas stream being dried.

BRIEF DESCRIPTION OF THE DRAWINGS

Three embodiments of the present invention are shown in the drawings.

DETAILED DESCRIPTION

Figure 1:
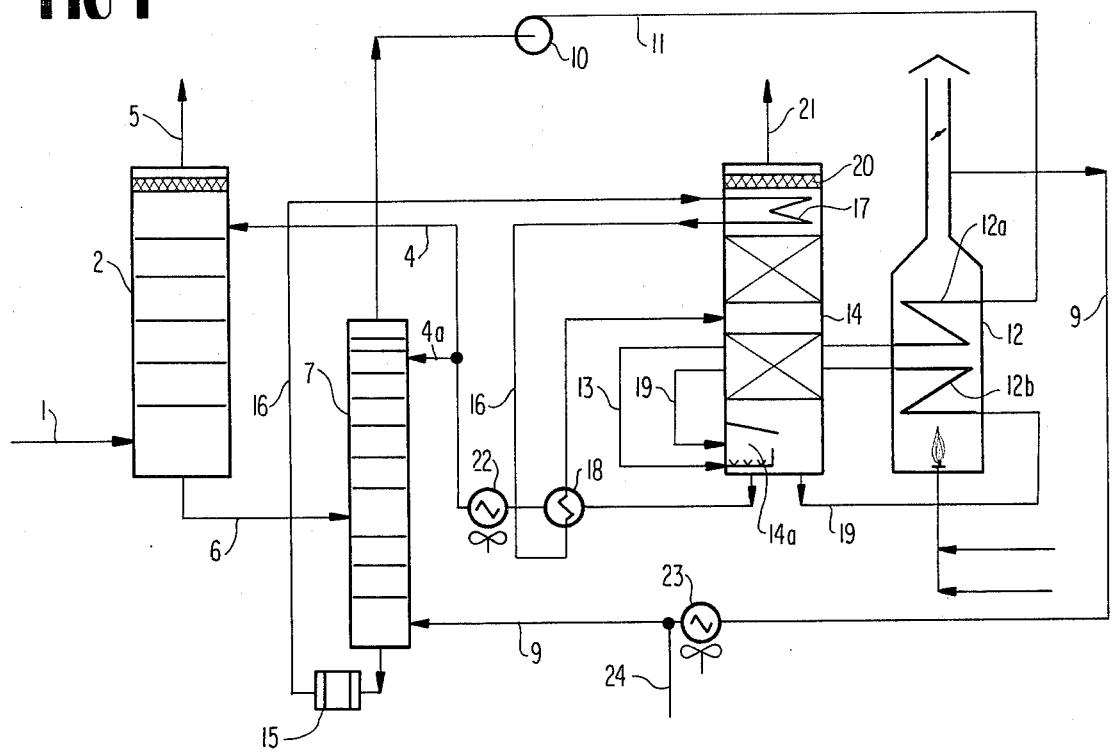
FIG. 1 represents a first embodiment of the process according to the invention, using flue gas to remove moisture from the glycol in a regeneration column.

The present invention relates to reconcentration of glycol which has been used to remove moisture from moist natural gas. The term glycol as used herein refers primarily to the preferred glycol for the practice of this invention which is triethylene glycol. It should be understood, however, that the term glycol also includes other glycols such as, for example, diethylene glycol (most particularly when using the glycol injection method which is hereinafter described in detail), tetraethylene glycol and monoethylene glycol.

The instant invention involves two stage removal of moisture from glycol being reconcentrated. Hot flue gas is used in an initial stage of water removal from glycol. Whereas the moist glycol is concentrated from the initial concentration, which is for example at 92 to 96 percent by weight glycol, up to about 99.0 to 99.2 percent, by the thermal regeneration, a further concentration up to 99.99 percent glycol is achieved by the stripping with flue gas or hydrocarbon gas in accordance with the invention. It is advantageous to work with 99.2 to 99.9 percent by weight glycol. The contact between the moist glycol and the stripping gas expediently takes place in a counter-current arrangement, by which low residual water contents in the glycol are encouraged. The stripping gas flowing in counter-current contact with the moist glycol reduces the water vapor partial pressure above the partially regenerated glycol to a very low value. This causes a shift in equilibrium between the gas phase and the liquid phase, so that additional water passes from the partially regenerated glycol and into the gas phase and a very low water content remains in the glycol. The great reduction in the residual water content by counter-current stripping of a glycol which is already thermally preconcentrated is due firstly to the favorable mass transfer between liquid phase and gas phase with the counter-current contact and secondly to the fact that the driving force of the water transition into the gas phase, as a result of the injection of stripping gas, is greater when the major part of the water contained in the glycol has already been previously removed by the action of heat.

The amount of stripping gas which is necessary depends on the residual water content of the glycol and stripping gas, the stripping gas temperature and the effectiveness of the contact between stripping gas and glycol. Generally speaking, the amount of stripping gas when there is counter-current contact with glycol is in the range from 4 to 100 $Nm^3$ of stripping gas per cubic meter of glycol, advantageously in the range from 15 to 50 $Nm^3$ of stripping gas per cubic meter of glycol.

Flue gas can serve both to initially heat the glycol and as a stripping gas for the glycol. Flue gas is available in sufficient quantity from the reboiler, which serves for heating up the moist glycol to the reconcentration temperature of 100° to 210° C. After drying, flue gas consists essentially of inert gas, namely nitrogen, carbon dioxide and traces of oxygen.

The hot flue gas is advantageously cooled to a temperature in the range from +5° to 75° C., preferably 20° to 60° C., dried by contact with glycol, and the dried flue gas is heated to a temperature in the range from 100° to 300° C., advantageously 140° to 210° C., and then used as stripping gas for the reconcentration of the glycol. The hot flue gas from the reboiler, depending on the utilization of heat therein, is available at a temperature from 300° to 600° C., for example, at 500° C. Since it is generally derived from the burning of natural gas, it contains substantial amounts of water vapor, which prohibit the immediate use of the flue gas as a stripping gas. The flue gas is consequently first of all dried with glycol, after having been cooled to a temperature in the range from 25° to 70° C. The drying is preferably effected in a small column, e.g., a plate-type column. The dried flue gas is then heated and introduced into the bottom of a regeneration column. As it rises in the regeneration column, the flue gas becomes charged with water vapor and can be directly blown off into the atmosphere at the top of the column.

The flue gas is preferably initially treated with the moist glycol from the natural gas drying operation and thereafter dried with a reconcentrated glycol cooled to a temperature in the range from 20° to 80° C. The moist glycol, resulting from this flue gas drying step is preferably filtered, heated to a temperature in the range from 100° to 210° C., and reconcentrated. As a consequence of this two-stage drying of the flue gas with moist glycol and dried glycol, the consumption of dried glycol for drying the flue gas is restricted to a minimum quantity, since the dried glycol is only used for the finish drying of the flue gas. The glycol from the two drying stages is subjected to a separation of solids, e.g., to a filtration, for the purpose of removing from the glycol any solid impurities possibly washed out of the flue gas. The glycol is then preheated in the usual way and supplied to the regeneration column.

Water is advantageously removed by condensation from the flue gas by cooling the flue gas to 5° to 75° C. to separate the water from the flue gas. When the flue gas is subsequently dried with glycol, it is then only necessary for a correspondingly smaller quantity of water to be removed from the flue gas, so that the amount of water to be driven off in the regeneration of the glycol is accordingly insignificantly increased.

After the flue gas has been dried, it is expediently heated by heat exchange with the hot flue gas. This heat exchange may take place directly in the reboiler or even in a heat exchanger, which is arranged in the hot flue gas pipe downstream of the reboiler. The flue gas is heated to such a temperature that it can, in the regeneration of the glycol, absorb a maximum amount of water vapor. The flue gas is not however, heated to such a temperature that the glycol is thermally decomposed on contact with the hot flue gas.

In accordance with another procedure for carrying out the process in accordance with the invention, the natural gas treated with glycol is cooled to a temperature in the range from −40° to +5° C., to form a condensate. The condensate so formed is then separated from the dried natural gas, a part of the hydrocarbon phase of the condensate is expanded and the hydrocarbon gas present after the expansion is used as stripping gas in the reconcentration of the glycol. The treatment of the natural gas with glycol can, for example, take place in a plate-type column, in which the water vapor from the natural gas is absorbed by dried glycol. However, the treatment with glycol can also be carried out in such a way that the dried glycol is sprayed as a hydrate inhibitor into the natural gas stream and the water-containing glycol is again separated out after having been cooled to low temperature. The condensate which forms with the cooling generally consists of moist glycol and a liquid hydrocarbon phase. The stripping gas is obtained from this condensate by expansion of part of the hydrocarbon phase. The volatile hydrocarbons, such as methane, ethane and propane escape from the liquid hydrocarbon phase with the expansion and are practically free from moisture, since even with formation of an aqueous condensate in the low temperature stage, the solubility of water in the hydrocarbon phase is extremely small. Thus, the expansion gas is also obtained in practically dry form. The gas which is formed by the above-described three-phase separation has a high methane content and in addition contains higher gaseous hydrocarbons, such as ethane, propane, butane, etc., and possibly also hydrogen. This gas occurs as a by-product with the low-temperature treatment of pre-dried or undried natural gas, and the use thereof as a stripping gas consequently does not decrease the production of the dried natural gas.

The hydrocarbon phase is preferably expanded to a pressure which is in the range from 1 to 4 atmospheres absolute, i.e., to a pressure which is greater than the pressure of the glycol column at the position of introduction of the stripping gas into the regeneration column. It is obvious that an expansion to below 1 atmosphere absolute is also possible, if the regeneration column is operated under vacuum.

The hydrocarbon gas is preferably heated to a temperature in the range from 90° to 210° C., and it is then introduced as stripping gas into the regeneration column. As a result of heating the stripping gas, it is assured that, when the gas comes into contact with the moist glycol, a maximum quantity of moisture can be absorbed, so that a best possible drying action is produced. On the other hand, the temperature of the stripping gas is not so high that there is a partial decomposition of the glycol and hence the need to supplement glycol is avoided. The theoretical decomposition temperatures of triethylene glycol and diethylene glycol are $-207°$ C. and $-165°$ C., respectively.

Provision is further made for the condensate to be separated from the dried natural gas under a pressure in the range from 20 to 80 atmospheres absolute, advantageously 40 to 60 atmospheres absolute. This is the pipeline pressure under which the dried natural gas is delivered from the plant. Since the liquid hydrocarbon phase is likewise under this pressure, it has consequently to be expanded from this pressure to somewhat higher than the operating pressure of the glycol regeneration column, so as to liberate the dissolved hydrocarbon gases and have them available below the pressure necessary for the glycol stripping.

In accordance with one embodiment of the process according to this invention, provision is made for water to be absorbed with dried glycol from the moist natural gas and for the natural gas to be cooled first by heat exchange with the undried cool natural gas feed and then with a low-temperature refrigerant to a temperature in the range from $-40°$ to $+5°$ C. This low temperature separation of hydrocarbons, following the usual drying with glycol, is used with natural gas which contains such a content of higher hydrocarbons that the danger exists that the temperature in the natural gas pipelines will not reach the hydrocarbon dew point and that the hydrocarbons will not be separated out. The cooling of the natural gas to a temperature in the range from $-40°$ to $+5°$ C. necessitates the use of a refrigerating plant, but also ensures the separation of the hydrocarbons without expansion.

With another embodiment of the process according to this invention, dried glycol is injected into the natural gas, which is somewhat below the well head pressure, the gas is cooled by heat exchange with the dried natural gas expanded to pipe pressure and then, by expansion to the pipe pressure, preferably to a pressure in the range from 20 to 80 atmospheres absolute, to a temperature in the range from $-40°$ to $+5°$ C. The moist glycol is thus separated from the hydrocarbon phase of the condensate and some of the hydrocarbon phase is further expanded. With this form of the process, the considerable well pressure of the natural gas of, for example, 80 atm. abs. or more, is utilized, and the natural gas is cooled to such an extent by the expansion from this pressure to the pipeline pressure that the liquid hydrocarbons and water condense and are separated. The moist glycol is separated from the hydrocarbon phase and is supplied to the glycol regeneration stage. Some of the hydrocarbon phase is expanded to a pressure somewhat higher than the glycol regeneration pressure, and the hydrocarbon gas phase which is thereby formed is used, after heating, as stripping gas for the regeneration of glycol.

The various embodiments of the present invention are more fully described with reference to the drawings. According to FIG. 1, the moist natural gas is introduced through a pipe 1 into an absorption column 2 and is dried in the latter in counter-current with glycol supplied through a pipe 4. The dried natural gas leaves the column 2 by way of a pipe 5. The moist glycol initially passes from the column 2 and through a pipe 6 to the central section of a flue gas drying column 7, to which cooled flue gas is supplied to the bottom end thereof through a pipe 9. The water vapor saturated flue gas is first of all prewashed and predried in the bottom section of the column with the moist glycol. It then flows into the top section of the column 7 and is thoroughly dried therein with dried glycol which is supplied through a pipe 4a. The dried cold flue gas is then forced by means of a blower 10 through a pipe 11 and a heater 12a into the reboiler 12 and then through a pipe 13 into the glycol regeneration column 14.

The moist glycol discharging from the bottom of the flue gas drying column 7 is freed from solid impurities in the filter 15 and then passes through a pipe 16 into a heat exchanger 17 at the top of the column 14 and to the heat exchanger 18, in which the glycol is preheated approximately to the regeneration temperature. The moist glycol is then fed into the middle section of the column 14. For maintaining the temperature in the column 14, some of the partially regenerated glycol is drawn off through a pipe 19, conducted through a heat exchanger 12b arranged in the reboiler 12 and fed back into the chamber 14a of the column 14. In the heat exchanger 12b, the temperature of the glycol is raised, for example, from 175° to 200° C. The partially regenerated glycol as thus heated passes into the separate chamber 14a in the sump of the column 14, whereas the partial stream conducted from the column 14 to the heat exchanger 12b is drawn off outside the said chamber, so that it is not possible to have a direct mixing of relatively cold and heated glycol in the sump of the column 14. The dry, heated flue gas introduced through the pipe 13 into the chamber 14a becomes loaded with water vapor as it ascends through the column 14. Glycol vapors and droplets are separated out from the gas flow by the heat exchanger 17 and the droplet separator 20. The moist flue gas leaves the colunn 14 by way of the stack 21 to enter the atmosphere.

The dried glycol leaves the column 14 at the base of the chamber 14a, is subjected to heat exchange with the moist glycol in the heat exchanger 18 and is thereafter cooled in the condenser 22 to the operating temperature of the absorption columns 2 and 7 and then supplied to the said columns by way of the pipes 4 and 4a, respectively. The flue gas which is used for the stripping is withdrawn from the stack of the reboiler 12 at a temperature of, for example, 500° C. and is supplied through pipe 9 to the flue gas drying column 7. Arranged in the pipe is a condenser 23, in which the flue gas is cooled, for example, from 500° C. to 40° to 50° C. The water thereby extracted by condensation is drawn off at 24.

Figure 2:
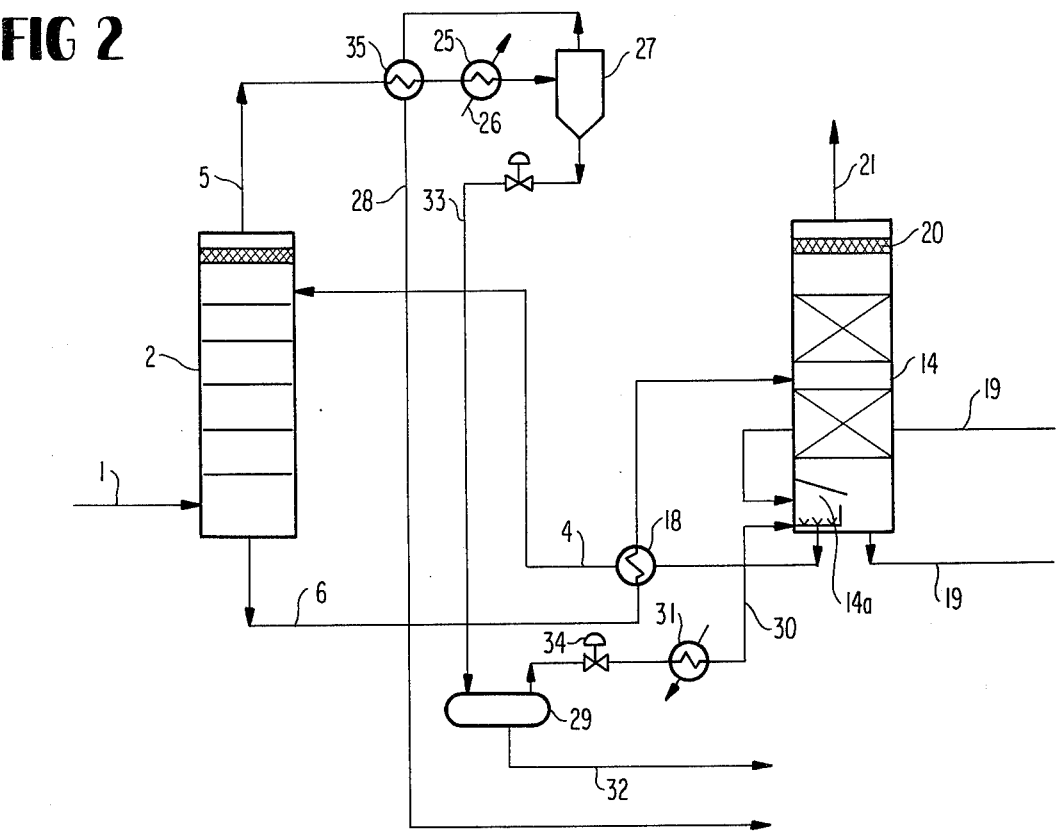
FIG. 2 represents a second embodiment of the process according to the invention, with hydrocarbon separation from dried natural gas by low temperature cooling subsequent to the drying of the moist gas stream and the use of separated hydrocarbon gas as stripping gas to remove moisture from glycol.

As regards the embodiment which is represented in FIG. 2, those parts of the installation which correspond to the parts in FIG. 1 are given the same reference numerals. The moist natural gas enters the absorption column 2 at 1 and is dried in said column with dried glycol which is supplied by way of the pipe 4. The moist glycol discharging at the base of the column 2 passes via the pipe 6 and the heat exchanger 18 to the central section of the regeneration column 14. The dried natural gas leaving the head of the column 2 passes by way of the pipe 5 to a heat exchanger 35, in which the gas is cooled by heat exchange with the cold gas, and then to a heat exchanger 25, in which it is cooled to, for example, −40° C. to +5° C., by a refrigerant introduced through a pipe 26. In the following vessel 27, the hydrocarbon condensate is separated from the natural gas, which now shows a low water vapor and hydrocarbon dew point, and is withdrawn through a pipe 28. The liquid hydrocarbon condensate flows from the vessel 27 by way of a pipe 33 into the three-phase separator 29. Some of the liquid hydrocarbons are expanded by a pressure-regulating valve 34 to a presssure which is somewhat above the operating pressure of the column 14. The gaseous hydrocarbons escape from the hydrocarbon condensate and flow through a pipe 30 to a heat exchanger 31, in which they are heated to the operating temperature of the column 14, and then into the chamber 14a of the column 14. The dry, heated hydrocarbon gas ascends in the column 14, becomes charged with water vapor and escapes through the stack 21 into the atmosphere, after entrained droplets of glycol have been kept back in the droplet separator 20. The heating of the glycol of the column 14 is achieved, in the same manner as with the embodiment of FIG. 1, in a reboiler (not shown), which is connected by the pipes 19 to the regeneration column 14. The hydrocarbon liquid remaining with the expansion in the three-phase separator 29 is drawn off as a by-product through a pipe 32.

Figure 3:
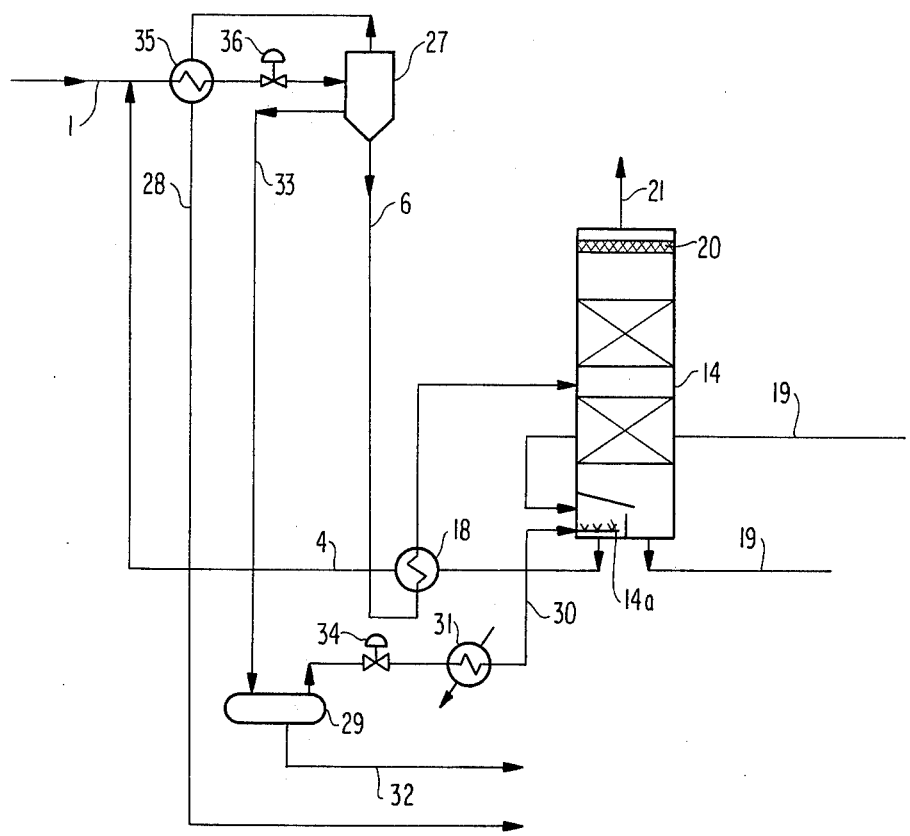
FIG. 3 represents a third embodiment of the process according to the invention, with injection of glycol into natural gas and expansion of the flow of this natural gas to provide a hydrocarbon gas which is used as stripping gas to remove moisture from glycol.

With the embodiment which is represented in FIG. 3, dried glycol supplied through the pipe 4 is injected as hydrate inhibitor into the natural gas which is in the pipe 1 and is below the well head pressure. Thereafter, the mixture flows through the heat exchanger 35, in which it is cooled by heat exchange with the cold natural gas expanded to pipeline pressure. The mixture is then cooled by further expansion at the throttle valve 36 to a temperature in the range from −40° to +5° C. Moist glycol and hydrocarbon condensate are separated in the separator vessel 27. The natural gas leaves the separator 27 with a very low water vapor content and hydrocarbon content by way of the pipe 28, is preheated in the heat exchanger 35 and is then discharged from the installation.

The moist glycol is withdrawn from the separator 27 through the pipe 6, is heated in the heat exchanger 18 to the working temperature of the regeneration column 14 and is then supplied to the central section of this column. The hydrocarbon liquid passes from the separator 27 by way of a pipe 33 into a collector 29, in which the gas pressure is released by the reducing valve 34 to somewhat above the operating pressure of the regeneration column 14. The gaseous hydrocarbons thus escape from the liquid phase and are introduced through a pipe 30 as stripping gas into the chamber 14a of the regeneration column 14, after having been heated in the heat exchanger 31. The hydrocarbon phase which has remained liquid in the collector 29 is drawn off through a pipe 32. The stripping gas ascending in the column 14 becomes charged with water vapor, is freed in the drop separator 20 from entrained glycol droplets and leaves the column via the stack 21. The temperature in the column 14 is maintained by the fact that the glycol is circulated through a reboiler (not shown), which is connected to the regeneration column 14 by the pipes 19. The dried glycol is withdrawn from the bottom the chamber 14a through the pipe 4, in which the heat exchanger 18 is arranged, is again fed to the natural gas pipe 1 and is injected into the said pipe.

The process embodiments of the present invention are further illustrated by the following Examples, which are not limiting of the present invention.

EXAMPLE 1

In order to dry $1 \times 10^6$ Nm$^3$/d of natural gas, which is supplied at 50 atm. abs. and 38° C. and is saturated with water vapor, to a dew point of −24° C., the gas stream is brought at the said temperature into contact with 99.7 percent triethylene glycol. 1.9 m$^3$/h of glycol are circulated through the absorption column. 240 Nm$^3$/h of flue gas are cooled to 40° C. and as a result 29 kg/h of water are separated out. Thereafter, the flue gas predried in this way is prescrubbed with the 1.9 m$^3$/h of 97 percent triethylene glycol discharging from the absorption column and is then thoroughly dried with 0.38 m$^3$/h of dried glycol. After being heated to 200° C., the flue gas which has been dried in this way is used as stripping gas in the regeneration of the moist glycol coming from the flue gas drying stage and in a quantity of about 120 Nm$^3$ of flue gas per cubic meter of glycol. The regeneration temperature is 200° C. 1.9 m$^3$/h of 99.7 percent triethylene glycol are drawn off from the regeneration stage.

EXAMPLE 2

$3.9 \times 10^6$ Nm$^3$/d of natural gas are dried with 7.4 m$^3$/h of 99.7 percent triethylene glycol. The 97 percent triethylene glycol discharging from the absorption stage is regenerated after heating at a temperature of 200° C. The natural gas from the absorption stage is cooled by heat exchange with refrigerant to −24° C. 11,200 kg/h of hydrocarbon condensate are separated out in a separator, while at the same time 160,000 Nm$^3$/h of natural gas are delivered into the long-distance pipeline. Such an amount of hydrocarbon condensate is expanded from the condensation pressure of 65 atm. abs. to 1.2 atm. abs. that 700 Nm$^3$/h of hydrocarbon gas, after heating to 200° C., can be introduced into the regeneration column as a stripping gas in a quantity of about 9.5 Nm$^3$/m$^3$ of glycol. At the same time, there remain, after the expansion, 10,600 kg/h of liquid hydrocarbons, which can be supplied as required for stabilization purposes. The regenerated glycol obtained when using hydrocarbon gas as stripping gas has a concentration of 99.7 percent and returns into the absorption stage.

EXAMPLE 3

200,000 Nm$^3$/h of natural gas, under a pressure of 130 atm. abs., have 600 kg/h of 99.7 percent triethylene glycol added thereto as hydrate inhibitor and are precooled to 0° C. The gas is then expanded to 65 atm. ats., 600 kg/h of triethylene glycol and 14,000 kg/h of liquid hydrocarbons separating out. The moist triethylene glycol is regenerated after heating to 200° C. After separating out the moist glycol, such a quantity of hydrocarbon liquid is expanded from 65 atm. abs. to 1.2 atm. abs. that 200 Nm$^3$/h of hydrocarbon gas are obtained, which are introduced as stripping gas into the regeneration column after having been heated to 200° C. After the partial expansion, there remain 13,870 kg/h of hydrocarbons, which are discharged or fed as required for stabilization. The regenerated triethylene glycol has a concentration of 99.7 percent and is used afresh for injection into the natural gas stream.

What is claimed is:

1. In a process for reconcentrating glycol which has been used to remove moisture from moist natural gas, whereby said natural gas is treated with glycol to absorb moisture from said natural gas and whereby the resulting moisture-containing glycol is reconcentrated by removal of moisture therefrom, the improvement which comprises:
   (a) heating said moisture-containing glycol to a temperature of from about 100° to 210° C. by heat exchange with flue gas from a reboiler; and thereafter
   (b) drying the flue gas from the reboiler by contact with glycol,
   (c) stripping additional moisture from said moisture-containing glycol with dried flue gas from said reboiler.

2. A process in accordance with claim 1 wherein said flue gas is cooled to a temperature of from about 5° to 75° C., dried by contact with glycol, and heated to a temperature of from about 100° to 300° C. and thereafter used to strip moisture from the moisture-containing glycol.

3. A process in accordance with claim 2 wherein said flue gas is cooled to a temperature of from about 20° C. to 60° C., dried by contact with glycol and thereafter heated to a temperature of from about 140° C. to 210° C.

4. A process in accordance with claims 1, 2 or 3 wherein
   (a) the flue gas, prior to use in the stripping step, is dried by an initial treatment with moist glycol obtained from the drying of natural gas and by a subsequent treatment with reconcentrated glycol having a temperature of from about 20° C. to 80° C.; and
   (b) the moist glycol formed in the process of drying the flue gas is reconcentrated after it is filtered and heated to a temperature of from about 100° to 210° C.

5. A process in accordance with claim 4 wherein the flue gas, after drying, is heated by heat exchange with the hot flue gas.

6. A process in accordance with claims 2 or 3 wherein, prior to drying the flue gas with glycol, water is condensed and separated from said flue gas by cooling said flue gas.

7. A process in accordance with claim 4 wherein, prior to drying the flue gas with glycol, water is condensed and separated from said flue gas by cooling said flue gas.

8. A process in accordance with claim 5 wherein, prior to drying the flue gas with glycol, water is condensed and separated from said flue gas by cooling said flue gas.

* * * * *